United States Patent [19]

Allain et al.

[11] 4,266,068

[45] May 5, 1981

[54] PREPARATION OF 1,2-TETRAMETHYLDICHLORO-DISILANE FROM HEXAMETHYLDISILANE AND METHYLCHLORODISILANE

[75] Inventors: Ronald J. Allain, Naperville, Ill.; Joseph P. Maniscalco, Sugar Land, Tex.

[73] Assignee: Nalco Chemical Company, Oak Brook, Ill.

[21] Appl. No.: 172,606

[22] Filed: Jul. 28, 1980

[51] Int. Cl.$^3$ .............................................. C07F 7/08
[52] U.S. Cl. .................... 556/430; 556/469
[58] Field of Search ......................................... 556/430

[56] References Cited

U.S. PATENT DOCUMENTS

| | | | |
|---|---|---|---|
| 3,398,177 | 8/1968 | Stewart | 556/430 X |
| 3,399,223 | 8/1968 | Atwell et al. | 556/430 |

OTHER PUBLICATIONS

"Monatshefte für Chemie", 105, pp. 671–683, 1974.
"J. Organomet. Chem.", 7, pp. 15–16, 1967.
"Redistribution of Organo Chlorosilanes", Advances in Chemistry Series, 23, 1959.
"Bull. Chem. Soc., Japan", 39, No. 8, p. 1820, 1966.
"Tetrahedron Letters", 45, pp. 5493–5497, 1966.

*Primary Examiner*—Paul F. Shaver
*Attorney, Agent, or Firm*—John G. Premo; Robert A. Miller

[57] ABSTRACT

An improved process for producing tetramethyldisilane by Lewis acid catalyzed redistribution of hexamethyldisilane with a crude mixture of methylchlorodisilane which comprises the distillation of the mixed redistributed product with collection of a middle distillate cut containing at least 95% pure tetramethyldichlorodisilane.

3 Claims, No Drawings

PREPARATION OF 1,2-TETRAMETHYLDICHLORO-DISILANE FROM HEXAMETHYLDISILANE AND METHYLCHLORODISILANE

INTRODUCTION

The preparation of 1,2-tetramethyldichlorodisilane has been accomplished by several different procedures. Amongst these are the reaction of hexamethyldisilane with anhydrous HCL and aluminum chloride catalyst systems. This reaction yields approximately 90% of the desired product but is very expensive since the starting product required is a hexamethyldisilane material. Reference to the synthesis of this material using the above mentioned procedure can be found in an article appearing in Tetrahedron Letters 45, 5493–5497, (1966) entitled *ALUMINUM CHLORIDE CATALYZED REACTIONS OF ORGANO SILICONE COMPOUNDS II. FASILE SYNTHESIS OF ALKYL CHLOROSILANES, -GERMANES, AND -STANANES.*, which article is incorporated in this application by reference.

Another procedure for accomplishing the same synthesis includes the reaction of hexamethyldisilane with acetyl chloride under aluminum chloride catalysis. This procedure is also outlined in the above reference and incorporated article. Again this synthesis procedure suffers from the fact that a hexamethyldisilane must be used as a starting material to accomplish the synthesis giving relatively high yields of the desired tetramethyldichlorodisilane compound.

The simpler method of obtaining the desired compound would be to redistribute both chloro and methyl groups from the reaction of hexamethyldisilane and a mixture of methylchlorodisilane compounds. Such a redistribution is again outlined in the above referenced article, but is therein limited to the redistribution reaction between hexamethyldisilane and tetramethyldichlorodisilane with aluminum chloride catalysts to obtain a final product of pentamethylchlorodisilane.

If one were able to achieve a redistribution between hexamethyldisilane and a crude mixture of methylchlorodisilane in such a way as to obtain high yields of the desired tetramethyldichlorodisilane, one would have contributed to the art in regards to this kind of silane chemistry.

PRIOR ART

The redistributions of organo chlorodisilanes are relatively well known. In a series of textbooks published by the American Chemical Society, an article appears in the text *Metal-Organic Compounds*, #23—Advances in Chemistry Series, Sept., 1959, entitled *Redistribution of Organo Chlorosilanes*. This article reviews procedures which have been used in the past to equilibrate various methylchlorosilanes and introduces a new catalyst, sodium chloroaluminate, which accomplishes this equilibration reaction.

An article by Sacurigy, et al, published in the Bulletin of Chemical Society, Japan 39 #8, (1966), 1820, teaches that aluminum chloride can be used to catalyze reactions of organosilicone compounds to obtain a rapid redistribution of chlorodisilane. This article again emphasizes the redistribution which forms pentamethylchlorodisilane, and also teaches the redistribution of the trimethylsilyl radical in reactions with aromatic silane compounds. In a footnote it is pointed out that the choice of solvents can drastically effect the rate and equilibrium of such a redistribution reaction.

None of the above mentioned references teach the use of hexamethyldisilane with a crude mixture of methylchlorodisilanes to obtain the desired product, tetramethyldichlorodisilane. Another article appearing in the Journal, MONATSH, CHEM, 105 (4), 671–83 (1974), teaches the reaction of hexamethyldisilane with trimethylchlorosilane. This article teaches the synthesis of the product which is desired in the instant invention, but also teaches the reaction using trimethylchlorosilane which yields a mixture of silane and disilane compounds which would not be amenable to recycle and maximization of the yields of the desired product.

Other references are also available which teach aluminum chloride catalyzed reactions of organo silicone compounds, for example *J. ORGANO METAL. CHEM.*, 7 (2), 14–15 (1957), which teaches the use of aluminum chloride, acetyl chloride, and hexamethyldisilane, at various times and temperatures to yield a mixture of various methylchlorodisilane compounds. This reference again does not teach procedures to maximize the yield of the desired product of this invention.

THE INVENTION

In the process of producing tetramethyldichlorodisilane (TMDDS) by Lewis Acid catalyzed redistribution of hexamethyldisilane (HMDS) and a crude mixture of methylchlorodisilanes which produces the mixed redistribution product, the improvement which comprises the distilling of mixed redistribution product under conditions whereby there is produced light ends distillate, a middle distillate and heavy bottoms, recovering the middle distillate which contains about 95% by weight of TMDDS, and then recycling the light end and heavy bottoms obtained from the distillation back to the crude mixture of methylchlorodisilanes for continued redistribution reaction. The Lewis Acid Catalyst preferred in the redistribution of hexamethyldisilane with crude mixtures of methylchlorodisilanes is preferably aluminum chloride in anhydrous form. This catalyst is best used within a concentration range of from 1.0% to 10.0% (by weight) of the total quantity of hexamethyldisilane and crude methylchlorodisilane compounds present in the reaction.

As practiced, the instant invention may yield a 95% pure tetramethyldichlorodisilane product which is the product of a recovery of the middle distillate in a continuous process which both achieves the redistribution of methyl and chloro groups within the disilane compound as well as recovers highly purified tetramethyldichlorodisilane while simultaneously recycling both the light ends distillate obtained in the distillation as well as the heavy bottoms remaining in the distillation pot back to the crude mixture of methylchlorodisilanes used originally for the redistribution reaction. When practiced in the preferred mode, this reaction obtains at least a 95% pure tetramethyldichlorodisilane, recycles both heavy bottoms as well as light ends obtained from the distillation back to the crude methylchlorodisilane mixture originally used, and continuously adds hexamethyldisilane and aluminum chloride in such a way as to obtain the redistribution of methyl and chloro radical functionality on the disilane backbone of these molecules.

HEXAMETHYLDISILANE

The hexamethyldisilane used can be conveniently prepared by reacting methyl Grignard reagent with the same crude methylchlorodisilane mixture in such a manner as to use a slight excess of the methyl Grignard reagent in a preferred mixed solvent of tetrahydrofuran (THF) and the diethyl ether of tetraethylene glycol (DETEG) which allows maximum yields of the hexamethyldisilane without the contributing complication of precipitated magnesium chloride by-product. This reaction produces hexamethyldisilane in excellent yields which provides a source of this material from the same crude mixture of methylchlorodisilanes as is used to obtain the redistributed product of the invention.

THE METHYLCHLORODISILANE

Byproduct Streams of methylchlorodisilane are readily obtainable on a commercial scale. These streams can be further purified by either a flash distillation topping of light end materials or a middle cut distillation of materials which tend to yield a material having the average stoichiometry represented by the following formula; $(CH_3)\rightarrow_{2.5}Si_2Cl_{3.5}$. The crude material may be distilled with collection of materials distilling between 135° C. to about 160° C. This fraction is primarily represented by the average stoichiometric formula previously mentioned. Materials that distilled prior to the initial collection point at 135° C. are normally and generally monosilane compounds of chloro, methyl substitution and simply would not yield the disilane compounds which are desirable in the instant invention. The materials remaining after the 165° C. boiling point maximum has been achieved normally would contain polysilane methyl, chloro compounds and again would not yield the disilane compounds of interest on catalytic redistribution with hexamethyldisilane.

A simple flash distillation which removes only those compounds boiling below 135° C. can also be accomplished. The crude stream obtained from commercial sources contains little of the polysilane compound previously mentioned and therefore a flash distillation with collection of materials above a boiling point of 135° C. can accomplish the isolation of a methylchlorodisilane mixture of compounds which is sufficiently pure to yield the starting materials used in the instant invention. As mentioned above, the preferred mixture of crude methylchlorodisilane has the average stoichiometry given in the formula of the previous paragraph.

THE LEWIS ACID CATALYST

As previously taught, and mentioned in the prior art, Lewis Acid Catalysts in general function to accomplish a faster and more efficient equilibration reaction between hexamethyldisilane and the chloromethyldisilane compounds. Many Lewis Acid Catalysts have been attempted and all have achieved some degree of equilibration. Examples include anhydrous stannic chloride, anhydrous magnesium chloride, anhydrous aluminum chloride, and anhydrous methylated aluminum compounds including trimethyl aluminum, dimethylchloro aluminum, methyldichloroaluminum as well as other alkyl aluminum compounds.

The preferred operation in the instant invention is the use of anhydrous aluminum chloride at anywheres from 1.0 to 10.0 weight percent based on the total amount of disilane compounds present in the mixture to be equilibrated. The rate of the equilibration seems to be related to the amount of aluminum chloride present during the equilibration. 1% aluminum chloride does accomplish an equilibration, but the yields are not commercially attractive. Five (5) weight percent aluminum chloride also doesn't achieve the high yields necessary to accomplish commercial utilization of aluminum chloride as the catalyst in this equilibration reaction. Ten (10) wt% aluminum chloride does accomplish the goal of achieving between a 70 and 80% yield of the desired tetramethyldichlorodisilane compound along with other materials composed primarily of pentamethylchlorodisilane and 1,1,2-trimethyltrichlorodisilane.

Another successful catalyst is composed of methyl aluminum compounds, either totally methylated or partially methylated, containing chloride radicals. As an example the trimethylaluminum compound achieves a high yield of the desired reaction equilibration products by using as little as 2 wt% catalyst. The alkyl aluminums have the advantage that less byproducts are made than are made by using aluminum chloride catalysts, however all three aluminum catalysts, i.e., aluminum chloride, trimethyl aluminum, and methyl aluminum sesquichloride, did give the same byproducts, those being chloropentamethyldisilane and 1,1,2-trichlorotrimethyldisilane. The other disadvantage to using the methylaluminum catalyst is the sensitivity of these catalysts to air and moisture and the hazardous nature involved in handling these materials.

The reaction can be carried out in either a solvent system composed of aromatic solvents such as benzene, toluene xylene and the like, or can be carried out in other appropriate solvent systems. There are some solvent systems which do not give desired equilibration reaction. As an example, both chloroform and dimethylformamide failed to yield the desired products when they were used as solvent systems for this equilibration. The same negative result was obtained when acetonitrile was attempted as a solvent for this system.

The preferred operation is the use of a system which does not add additional solvent. This "neat" system is composed simply of the hexamethyldisilanes and the crude or distilled crude mixture of methylchlorodisilane materials. To this mixture of disilane compounds is added the catalyst of choice followed by subsequent heating until the desired products are obtained.

The product mixture obtained in the original equilibration normally yields between 70 to 80% of the tetramethyldichlorodisilane compound along with 20 to 30% of a mixture of other chloromethyl compounds.

THE DISTILLATION

The mixture of products, obtained as previously mentioned, require a distillation step to purify and isolate from the mixture of equilibrated compound the desirable tetramethyldichlorodisilane materials. This distillation step is rather straightforward and simply allows the recovery of the desired compound and the recycle of both the light end materials, primarily composed of pentamethylchlorodisilane, and the heavy bottoms from the distillation vessel, primarily composed of 1,1,2-trimethyltrichlorodisilane. Both the light end overhead distillate and the bottoms of the still are recyclable and intermixable with the original crude methylchlorodisilanes streams and subject to further catalyzed redistribution of methyl and chloro functional groups. The distillation accomplishes a purity and yield of 1,1,2,2-tetramethyldichlorodisilane of at least 95 weight percent, and has the capability under close control of accomplishing a purity of 99 plus weight percent of the desired compound.

By varying the reflux rate, 99 percent purity 1,1,2,2-tetramethyldichlorodisilane is obtainable.

The process may be made continuous by taking a middle cut of desired purity of the tetramethyldichlorodisilane and recycling both the overhead and still bottoms remaining in a continuously operated distillation unit. The recycled materials would be intermixed with the crude methylchlorodisilanes, either distilled or topped, and would contribute to increased over all yields subsequent to the recycling.

EXAMPLES

Examples of the instant invention are as follows:

EXAMPLE 1.

A mixture of crude methylchlorodisilane compounds were distilled using a twelve foot two inch ID glass column containing 8 ft. of stainless steel protuded packing. Reflux rate was controlled by a Flexopulse timer and a magnetic distilling head. A 22 l glass flask served as the distillation pot.

About 17 l. of the mixture was charged into the glass pot. Reflux rates varied from 0.2 to 3 with a maximum take-off of distillate of about 0.7 gallons/hour. All silanes collected below 135° C. boiling point were tagged as "lights" (mainly methylchloromonosilanes). Silanes boiling from 135° C. to about 160° C. were collected and called distilled "heavies" or the disilane fraction. Remaining silanes in the pot contained unidentified higher boiling silanes (probably polysilanes).

The column was kept under inert gas at all times since chlorodisilanes, in general, are air and moisture sensitive.

The materials obtained from this distillation had an average stoichiometry of $(CH_3)\rightarrow_{2.5}Si_2Cl_{3.5}$.

EXAMPLE 2.

Into a 22 l. glass flask fitted with stirrer and condensor, 3.33 kg. of HMDS, 6.63 kg. of distilled mixtures, and 1.99 kg. of anhydrous AlCl$_3$ was added. The reaction pot was maintained under an inert gas at all times. The mixture was then heated to reflux (about 128° C. pot temperature) and allowed to reflux for two hours. During this time, the pot temperature rose to a plateau of about 140° C. The mixture was allowed to cool to ambient temperature. To the reaction mixture, 1.35 kg. of anhydrous acetone was added with stirring for over an hour. Temperature rose to about 50° C. in the pot. After cooling to ambient, the mixture was then filtered in a large glove bag under inert gas. The filter cake was then washed with 2.57 kg. of hexane to remove residual product. Analysis of the filtrate revealed about 80% yield of 1,1,2,2-tetramethyldichlorodisilane, with the remainder being pentamethylchlorodisilane and 1,1,2-trimethyltrichlorodisilane.

EXAMPLE 3.

Distillation equipment is the same as that used in distilling the mixture. About 17 l. of the equilibrated mixture is heated and brought to reflux. Hexane was stripped out and then, by using various reflux rates, the 1,1,2,2-tetramethyldichlorodisilane was distilled to obtain a 98% purity. Pentamethylchlorodisilane and 1,1,2-trimethyltrichlorodisilane can be recycled back to a subsequent equilibration reaction. Typical column conditions needed to obtain high purity 1,1,2,2-tetramethyldichlorodisilane are a reflux rate of 10, 0.1 gallons/hour distillate take-off, pot temperature of about 165° C., and 150° C. overhead temperature. The distillation must be kept under inert gas.

A series of experiments were run evaluating the equilibration reaction using the 3 types of methylchlorodisilane mixtures that can be obtained from the commercially available crude byproduct sidestream. Hexamethyldisilane made from the undistilled mixture was equilibrated with the undistilled sidestream itself. Hexamethyldisilane synthesized from a distilled fraction of the sidestream was equilibrated with that same distilled fraction of the sidestream. The distilled sidestream could be a middle cut obtained from the distillation of this crude sidestream of methylchlorodisilanes.

Yields calculated and product purity obtained by treating each of these materials in the manner outlined may be found in Table I.

TABLE I

| | EQUILIBRATION DATA FROM UNDISTILLED, DISTILLED, AND TOPPED SIDESTREAM "MIXTURES" | | | | | | | | | |
|---|---|---|---|---|---|---|---|---|---|---|
| | Moles Charged | | | | Mole Ratios | | % Yield | Product Purity % | | |
| Type of Sidestream "Mixtures" | Cl$^-$ | HMDS | Mole Ratio Cl$^-$/HMDS | Moles Produced | A HMDS | A Cl$^-$ | Based on HMDS | B | A | C |
| Undistilled | 125.8 | 23.2 | 5.40 | 30.9 | 1.33 | 0.25 | 57 | 7.1 | 56.3 | 5.1 |
| Distilled | 103.7 | 21.2 | 4.89 | 39.4 | 1.86 | 0.38 | 80 | 6.4 | 84.2 | 3.7 |
| Topped | 116.2 | 22.9 | 5.07 | 40.3 | 1.76 | 0.35 | 75 | 4.2 | 79.1 | 6.9 |

A = 1,1,2-tetramethyldichlorodisilane
B = pentamethylchlorodisilane
C = 1,1,2-trimethyltrichlorodisilane As the data in Table I indicates, the highest product purity obtained is with a distilled cut of the sidestream mixture of methylchlorodisilanes equilibrated with hexamethyldisilane which is, in turn, synthesized from that same distilled fraction of the sidestream mixture of crude methylchlorodisilanes. Analysis of these products are completed using standard gas chromatagraphic techniques.

Having described and specifically pointed out the invention, we claim:

1. In the process of producing tetramethyldichlorodisilane (TMDDS) by Lewis acid catalyzed redistribution of hexamethyldisilane (HMDS) and a crude mixture of methylchlorodisilane which produces a mixed redistribution product, the improvement which comprises distilling the mixed redistribution product under conditions whereby there is produced a light ends distillate, a middle distillate and heavy bottoms, recovering the middle distillate which is about 95% pure TMDDS by weight and recycling the light ends distillate and heavy bottoms with the crude mixture of methylchlorodisilanes for continued redistribution.

2. The process of claim 1 wherein the recovery of 95% pure TMDDS and recycling the light ends distillate and heavy bottoms from the distillation back to the crude mixture of methylchlorodisilanes for continued redistribution reaction are done continuously.

3. The process of claim 1 wherein the Lewis acid catalyst is anhydrous aluminum chloride within the concentration range of 1.0 to 10.0 weight percent of the total quantity of HMDS and methyl chlorodisilane.

* * * * *